United States Patent [19]

Grosius et al.

[11] Patent Number: 5,210,199

[45] Date of Patent: May 11, 1993

[54] PROCESS FOR THE PREPARATION OF ALKYLIMIDAZOLIDONE (METH) ACRYLATE

[75] Inventors: Paul Grosius, Forbach; Didier Vanhoye, Petite-Rosselle, both of France

[73] Assignee: Atochem, Paris, France

[21] Appl. No.: 626,107

[22] Filed: Dec. 14, 1990

[30] Foreign Application Priority Data

Dec. 15, 1989 [FR] France ................. 89 16607

[51] Int. Cl.$^5$ ............... C07D 233/02; C07D 239/04; C07D 243/04; C07D 245/02
[52] U.S. Cl. .............. 548/324.1; 540/460; 540/492; 544/318
[58] Field of Search .............. 548/320, 324.1; 544/318; 560/217, 234; 540/460, 492

[56] References Cited

U.S. PATENT DOCUMENTS

| | | | |
|---|---|---|---|
| 2,871,223 | 1/1959 | Hankins et al. | 525/385 |
| 3,642,877 | 2/1972 | Jayawant | 560/217 |
| 4,150,234 | 4/1979 | Seltzer et al. | 548/312 |
| 4,301,297 | 11/1981 | Kametani et al. | 560/217 |
| 4,777,265 | 10/1988 | Merger et al. | 548/320 |

FOREIGN PATENT DOCUMENTS

0170730 10/1983 Japan.

*Primary Examiner*—Joseph Paul Brust
*Assistant Examiner*—Mary Susan H. Gabilan
*Attorney, Agent, or Firm*—Millen, White, Zelano & Branigan

[57] ABSTRACT

At least one (meth)acrylate is reacted with a heterocyclic alcohol (III) in the presence of at least one catalyst chosen from dialkyltin oxides and dialkyltin dialkoxides.

Alkylimidazolidone acrylates and methacrylates are known for the part they play in the constitution of polymers which can be used as coatings and adhesives and for the treatment of paper and textiles, and for their use as agents for the treatment of leather and in the production of emulsion paints.

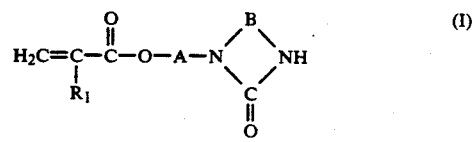

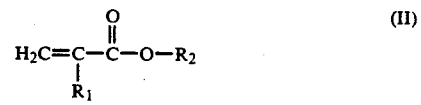

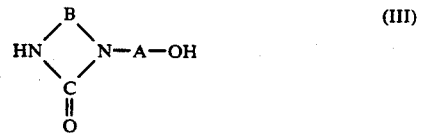

$R_1$ = H, $CH_3$; A, B = straight or branched chain alkylene group containing from 2 to 5 carbon atoms.

24 Claims, No Drawings

PROCESS FOR THE PREPARATION OF ALKYLIMIDAZOLIDONE (METH) ACRYLATE

BACKGROUND OF THE INVENTION

The present invention relates to a new process for the synthesis of alkylimidazolidone acrylates and methacrylates.

Alkylimidazolidone acrylates and methacrylates are known because of the part they play in the constitution of polymers used as coatings and adhesives, and for the treatment of paper and of textiles, especially from U.S. Pat. No. 2,871,223, and for their use as agents for leather treatment and in the production of emulsion paints. However, until now there was no process for the synthesis of these products which was selective and easy to scale up to an industrial scale. Such a process constitutes, therefore, the objective of the present invention.

SUMMARY OF THE INVENTION

The subject of the present invention consists therefore of a process for the preparation of a compound of formula:

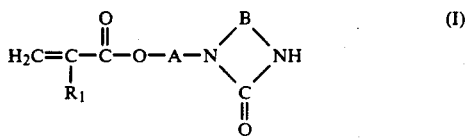

in which:
$R_1$ is chosen from hydrogen and the methyl group, and
A and B are chosen from straight or branched chain alkylene groups containing from 2 to 5 carbon atoms, by reaction of at least one (meth)acrylate of formula:

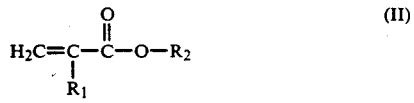

in which $R_1$ has the abovementioned meaning and $R_2$ is an alkyl radical containing from 1 to 4 carbon atoms, with a heterocyclic alcohol of formula:

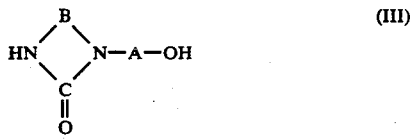

in which A and B have the abovementioned meaning, in the presence of at least one catalyst chosen from dialkyltin oxides, dialkyltin dialkoxides and dialkyltin diesters.

Examples of reactants of formula (II) which may be mentioned are especially methyl, ethyl, n-propyl, isopropyl, n-butyl, isobutyl and tert-butyl acrylates and methacrylates and their mixtures in all proportions. An example of heterocyclic alcohol of formula (III) which may be mentioned is especially 1-(2-hydroxyethyl-)imidazolidyl-2-one. Examples of catalysts which may be mentioned are especially di-n-butyltin oxide, di-n-octyltin oxide, bis-(di-n-butyl)acetoxytin and their mixtures in all proportions.

The quantity of catalyst which is employed for implementing the process according to the invention is generally approximately between 0.05 and 2 mol%, preferably between 0.1 and 1 mol% per mole of heterocyclic alcohol of formula (III).

The reaction of the process according to the invention may be carried out in the presence of an excess of either of the reactants. It is recommended, however, that the molar ratio (meth)acrylate of formula (II)/heterocyclic alcohol of formula (III) should be approximately between 1.1 and 6.0, preferably between 2.0 and 5.0. When operating with a large molar excess of (meth)acrylate relative to the heterocyclic alcohol, a solution of compound of formula (I) in the (meth)acrylate will be obtained as a result of the reaction, and this can be employed directly for some applications such as the preparation of paints and coatings or else leather treatment.

The reaction of the process according to the invention is preferably carried out in the presence of at least one polymerization inhibitor employed, for example, in a proportion of 0.05% to 0.5% by weight based on the weight of the heterocyclic alcohol of formula (III). Examples of polymerization inhibitors which may be used are especially phenothiazine, hydroquinone methyl ether, N,N-diethylhydroxylamine, nitrobenzene, di-tert-butylcatechol, hydroquinone, p-anilinophenol, di-(2-ethylhexyl) octylphenyl phosphite and their mixtures in all proportions.

The reaction of the process according to the invention is carried out preferably at a pressure not exceeding atmospheric pressure, for example at a pressure of between 0.3 and 1 bar. It is carried out by mixing the (meth)acrylate of formula (II) and the heterocyclic alcohol of formula (III) and by heating the reaction mixture under total reflux, generally at a temperature of approximately between 70° C. and 120° C., preferably between 80° C. and 110° C., this temperature being obviously dependent on the precise nature of the alcohol and of the (meth)acrylate.

In implementing the process according to the invention it is recommended to reach a maximum dehydration before the addition of a catalyst, so as to avoid the deactivation of the latter by water. This result can be achieved, for example, by heating the initial mixture of (meth)acrylate of formula (II), of heterocyclic alcohol of formula (III) and, if appropriate of the polymerization inhibitor under total reflux, and by then separating off the azeotrope of (meth)acrylate and water by distillation. At this stage, after separation of the distillate and after sufficient cooling of the reaction mixture to condense all the vapor present in the column, the catalyst may be introduced into the reaction mixture.

The duration of the reaction according to the invention, which obviously depends on reaction conditions such as temperature, pressure and the quantity of catalyst employed, is generally approximately between 1 and 10 hours.

The reaction mixture is therefore heated under total reflux until the head temperature reaches the distillation temperature of the azeotrope of the (meth)acrylate and of the alcohol of formula $R_2OH$, formed by the reaction. This distillation temperature is approximately 65° C. where the azeotrope of methanol and methylmethacrylate is concerned, approximately 82° C. where the azeotrope of ethanol and ethyl methacrylate is concerned and approximately 84° C. where the azeotrope of ethanol and ethyl acrylate is concerned. Whatever the compounds present in the column, the head temperature should be kept below approximately 120° C., if need be by employing a reduced pressure, so as to avoid any risk of polymerization. It is generally desirable to reduce the pressure gradually after the separation by distillation of the azeotrope of alcohol formed by the reaction and of (meth)acrylate.

The possible excess (meth)acrylate may then be removed by evaporation (so-called stripping operation) so as to isolate the compound of formula (I) from the reaction mixture, generally in the solid state: thus, 1-(2-hydroxyethyl)imidazolidyl-2-one acrylate is a white crystalline solid with a melting point of 43° C., soluble in cold ketones, alcohols, aromatic hydrocarbons and water, insoluble in cold saturated hydrocarbons and precipitating at 0° C. from ethyl acrylate. 1-(2-Hydroxyethyl)imidazolidyl-2-one methacrylate is a white crystalline solid with a melting point of 47° C., which has the same solubility properties as the preceding compound. At the end of the stripping operation the crystalline solid product may be additionally purified by washing with a light alcohol such as methanol and/or with a petroleum ether, followed by filtration and drying.

The isolation of the compound of formula (I) can also be carried out by partial stripping of the (meth)acrylate, followed by crystallization at a temperature which is sufficiently low (preferably lower than or equal to 0° C.) and for a period that is sufficiently long (capable of reaching 15 hours), and then filtration followed by the purification stages described above.

Finally, a third method for isolating the compound of formula (I) from the solution containing it consists in carrying out an extraction with water followed by a phase separation, stripping of the (meth)acrylate and the purification stages described above.

Thus, the process according to the invention makes it possible to obtain, either pure or in form of solution in the (meth)acrylate, a high yield of the compound of the formula (I): in the case of 1-(2-hydroxyethyl)imidazolidyl-2-one methacrylate the yield commonly exceeds 94% and can reach 99%. In the case of 1-(2-hydroxyethyl)imidazolidyl-2-one acrylate the yield commonly exceeds 80% and can reach 88%.

The following examples are given by way of illustration without limiting the present invention.

EXAMPLE 1

Into a 0.5-liter reactor operating at atmospheric pressure are introduced 450 g of methyl methacrylate stabilized with 250 ppm of hydroquinone methyl ether, 130 g of 1-(2-hydroxyethyl)imidazolidyl-2-one, 1.24 g of di-n-butyltin oxide and 0.2 g of phenothiazine. The reaction mixture is heated to boiling. Initially heterogeneous, the mixture becomes translucent after an hour while the azeotrope of methanol and of methyl methacrylate distills overhead at a temperature of 65° C. After 5 hours and 10 minutes of the reaction the pressure is gradually reduced to 0.6 bar. The reactor's contents are then cooled to room temperature and are then drained. The molar yield of 1-(2-hydroxyethyl)imidazolidyl-2-one methacrylate (also named 1-(2-methacryloyloxyethyl)-imidazolidin-2-one) as determined by quantitative estimation using high-performance liquid chromatography, is 98.4%. A solution of 1-(2-hydro-xyethyl)imidazolidyl-2-one methacrylate at a concentration of approximately 40% in methyl methacrylate is thus obtained, from which the reaction product can be isolated if required.

EXAMPLE 2

The experimental procedure of Example 1 is reproduced except that di-n-butyltin oxide is replaced with 3.64 g of bisdibutyltin acetoxide (marketed by M & T Chimie) corresponding to 0.6 mol% relative to the alcohol, and that the reaction is continued for 6 hours and 30 minutes. The molar yield of 1-(-2-hydroxyethyl)imidazolidyl-2-one methacrylate is 96.7%.

EXAMPLE 3

Into a 0.5-liter reactor operating at atmospheric pressure are introduced 450 g of ethyl acrylate stabilized with 250 ppm of hydroquinone methyl ether, 130 g of 1-(2-hydroxyethyl)imidazolidyl-2-one, 2.48 g of di-n-butyltin oxide and 0.5 g of phenothiazine. The reaction mixture is heated to boiling. Initially heterogeneous, the mixture becomes translucent after an hour while the azeotrope of ethanol and of ethyl acrylate distils overhead at a temperature of 84° C. After 7 hours' reaction the pressure is gradually reduced to 0.6 bars. The reactor's contents are then cooled to room temperature and are then drained. The molar yield of 1-(2-hydroxyethyl)imidazolidyl-2-one acrylate, determined by quantitative estimation by high-performance liquid chromatography, is 86%. A solution of 1-(2-hydroxyethyl)imidazolidyl-2-one acrylate at a concentration of approximately 33% in ethyl acrylate is thus obtained, from which the reaction product can be isolated if desired.

What is claimed is:

1. A process for the preparation of a compound of formula I:

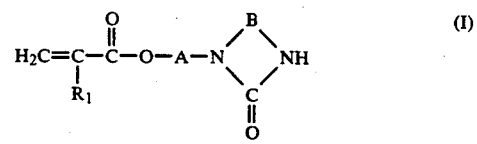

wherein:

$R_1$ is hydrogen or methyl, and

A and B are each a straight- or branched chain alkylene group containing 2 to 5 carbon atoms, by reaction of at least one (meth)acrylate of formula II:

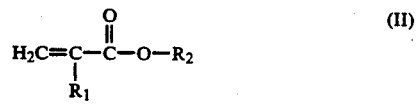

wherein $R_1$ has the above-mentioned meaning and $R_2$ is an alkyl radical containing from 1 to 4 carbon atoms, with a heterocyclic alcohol of formula III:

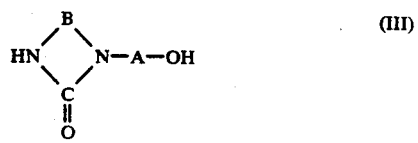

wherein A and B have the above-mentioned meaning, in the presence of a catalytic quantity of at least one catalyst which is a dialkyltin oxide, a dialkyltin dialkoxide, or a dialkyltin diester or mixtures thereof.

2. A process according to claim 1, wherein the catalyst is di-n-butyltin oxide, di-n-octyltin oxide, bis(di-n-butyl)acetoxytin, or mixtures thereof.

3. A process according to claim 1, wherein the catalyst is employed in a quantity of between 0.05 and 2 mol% per mole of heterocyclic alcohol of formula (III).

4. A process according to claim 1, wherein the molar ratio of (meth)acrylate of formula (II)/heterocyclic alcohol of formula (III) is between 1.1 and 6.0.

5. A process according to claim 1, wherein the reaction is carried out in the presence of at least one polymerization inhibitor.

6. A process according to claim 5, wherein the polymerization inhibitor is phenothiazine, hydroquinone methyl ether, N,N-diethylhydroxylamine, nitrobenzene, di-tert-butylcatechol, hydroquinone, p-anilinophenol, di-(2-ethylhexyl) octylphenyl phosphite, or mixtures thereof.

7. A process according to claim 6, wherein the polymerization inhibitor is employed in a proportion of 0.05% and 0.5% by weight based on the weight of the heterocyclic alcohol of formula (III).

8. A process according to claim 1, wherein the reaction is conducted for a period of between 1 and 10 hours.

9. A process according to claim 1, wherein the reaction is carried out at a pressure not exceeding atmospheric pressure.

10. A process according to claim 1, wherein the reaction is carried out at a temperature of between 70° C. and 120° C.

11. A process according to claim 3, wherein the catalyst is di-n-butyltin oxide, di-n-octyltin oxide, bis(di-n-butyl)acetoxytin, or mixtures thereof.

12. A process according to claim 4, wherein the catalyst is di-n-butyltin oxide, di-n-octyltin oxide, bis(di-n-butyl)acetoxytin, or mixtures thereof.

13. A process according to claim 5, wherein the catalyst is di-n-butyltin oxide, di-n-octyltin oxide, bis(di-n-butyl)acetoxytin, or mixtures thereof.

14. A process according to claim 6, wherein the catalyst is di-n-butyltin oxide, di-n-octyltin oxide, bis(di-n-butyl)acetoxytin, or mixtures thereof.

15. A process according to claim 11, wherein the reaction is carried out at a pressure not exceeding atmospheric pressure.

16. A process according to claim 14, wherein the reaction is carried out at a pressure not exceeding atmospheric pressure.

17. A process according to claim 9, wherein the reaction is carried out at a temperature of between 70° C. and 120° C.

18. A process according to claim 14, wherein the reaction is carried out at a temperature of between 70° C. and 120° C.

19. A process according to claim 15, wherein the reaction is carried out at a temperature of between 70° C. and 120° C.

20. A process according to claim 19, wherein the reaction temperature is not higher than the temperature of distillation of an azeotrope of the compound of Formula II and $R_2OH$.

21. A process according to claim 1, wherein said at least one catalyst is a dialkyltin dialkoxide or a dialkyltin diester or mixtures thereof.

22. A process according to claim 1, for the preparation of 1-(2-methacryloyloxyethyl)imidazolin-2-one from methylmethacrylate and 1-(2-hydroxyethyl)imidazolidine-2-one, wherein the catalyst is di-n-butyl tin oxide and the reaction is conducted in the presence of a polymerization inhibitor.

23. A process according to claim 1, for the preparation of 1-(2-methacryloyloxyethyl)imidazolin-2-one from methylmethacrylate and 1-(2-hydroxyethyl)imidazolidine-2-one, wherein the catalyst is (bis)dibutyl tin acetoxide and the reaction is conducted in the presence of a polymerization inhibitor.

24. A process according to claim 1, for the preparation of 1-(2-hydroxyethyl)imidazolidyl-2-one acrylate from ethyl acrylate and 1-(2-hydroxyethyl)imidazolidyl-2-one, wherein the catalyst is di-n-butyl tin oxide and the reaction is conducted in the presence of a polymerization inhibitor.

* * * * *